(12) United States Patent
Orszulak et al.

(10) Patent No.: US 7,648,499 B2
(45) Date of Patent: Jan. 19, 2010

(54) SYSTEM AND METHOD FOR GENERATING RADIO FREQUENCY ENERGY

(75) Inventors: James H. Orszulak, Nederland, CO (US); James W. McPherson, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 570 days.

(21) Appl. No.: 11/385,511

(22) Filed: Mar. 21, 2006

(65) Prior Publication Data

US 2007/0225698 A1    Sep. 27, 2007

(51) Int. Cl.
*A61B 18/18* (2006.01)

(52) U.S. Cl. ........................................... 606/34; 606/32

(58) Field of Classification Search ................... 606/34, 606/37–42, 45–52; 342/175; 361/157, 160, 361/182–184; 455/41.1, 66.1, 90.1, 106; 333/101, 175
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |

(Continued)

FOREIGN PATENT DOCUMENTS

DE    179607    3/1905

(Continued)

OTHER PUBLICATIONS

International Search Report EP 06000708.5 dated Apr. 21, 2006.

(Continued)

*Primary Examiner*—Michael Peffley
*Assistant Examiner*—Samantha Muro

(57) ABSTRACT

An electrosurgical generator is disclosed. The electrosurgical generator includes a power supply for generating a DC voltage. The electrosurgical generator also includes a first parallel inductor-capacitor circuit being driven by a first signal at a first predetermined frequency and a second parallel inductor-capacitor inductor-capacitor circuit driven by a second signal at the first predetermined frequency phase shifted 180°. The electrosurgical generator further includes a series inductor-capacitor resonant circuit operably connected in series with a primary winding of a transformer. The first and second parallel inductor-capacitor circuits are operably connected to the transformer, such that the first inductor-capacitor circuit generates a positive half sine wave and the second inductor-capacitor circuit generates a 180° phase-shifted positive half sine wave to generate a full sine wave in a secondary winding of the transformer.

20 Claims, 5 Drawing Sheets

U.S. PATENT DOCUMENTS

| | | |
|---|---|---|
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubivitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |

| | | | | | |
|---|---|---|---|---|---|
| 4,966,597 A | 10/1990 | Cosman | 5,451,224 A | 9/1995 | Goble et al. |
| 4,969,885 A | 11/1990 | Farin | 5,458,597 A | 10/1995 | Edwards et al. |
| 4,992,719 A | 2/1991 | Harvey | 5,462,521 A | 10/1995 | Brucker et al. |
| 4,993,430 A | 2/1991 | Shimoyama et al. | 5,472,441 A | 12/1995 | Edwards et al. |
| 4,995,877 A | 2/1991 | Ams et al. | 5,472,443 A | 12/1995 | Cordis et al. |
| 5,015,227 A | 5/1991 | Broadwin et al. | 5,480,399 A | 1/1996 | Hebborn |
| 5,024,668 A | 6/1991 | Peters et al. | 5,483,952 A | 1/1996 | Aranyi |
| 5,087,257 A | 2/1992 | Farin | 5,496,312 A | 3/1996 | Klicek |
| 5,099,840 A | 3/1992 | Goble et al. | 5,496,313 A | 3/1996 | Gentelia et al. |
| 5,103,804 A | 4/1992 | Abele et al. | 5,500,012 A | 3/1996 | Brucker et al. |
| 5,108,389 A | 4/1992 | Cosmescu | 5,500,616 A | 3/1996 | Ochi |
| 5,108,391 A | 4/1992 | Flachenecker | 5,514,129 A | 5/1996 | Smith |
| 5,122,137 A | 6/1992 | Lennox | 5,520,684 A | 5/1996 | Imran |
| 5,133,711 A | 7/1992 | Hagen | 5,531,774 A | 7/1996 | Schulman et al. |
| 5,151,102 A | 9/1992 | Kamiyama et al. | 5,534,018 A | 7/1996 | Wahlstrand et al. |
| 5,152,762 A | 10/1992 | McElhenney | 5,536,267 A | 7/1996 | Edwards et al. |
| 5,157,603 A | 10/1992 | Scheller et al. | 5,540,681 A | 7/1996 | Strul et al. |
| 5,160,334 A | 11/1992 | Billings et al. | 5,540,683 A | 7/1996 | Ichikawa |
| 5,167,658 A | 12/1992 | Ensslin | 5,540,684 A | 7/1996 | Hassler, Jr. |
| 5,190,517 A | 3/1993 | Zieve et al. | 5,556,396 A | 9/1996 | Cohen et al. |
| 5,196,008 A | 3/1993 | Kuenecke | 5,558,671 A | 9/1996 | Yates |
| 5,196,009 A | 3/1993 | Kirwan, Jr. | 5,569,242 A | 10/1996 | Lax et al. |
| 5,201,900 A | 4/1993 | Nardella | 5,571,147 A | 11/1996 | Sluijter et al. |
| 5,207,691 A | 5/1993 | Nardella | 5,573,533 A | 11/1996 | Strul |
| 5,230,623 A | 7/1993 | Guthrie et al. | 5,584,830 A | 12/1996 | Ladd et al. |
| 5,233,515 A | 8/1993 | Cosman | 5,588,432 A | 12/1996 | Crowley |
| 5,249,121 A | 9/1993 | Baum et al. | 5,596,466 A | 1/1997 | Ochi |
| 5,254,117 A | 10/1993 | Rigby et al. | 5,599,344 A | 2/1997 | Paterson |
| RE34,432 E | 11/1993 | Bertrand | 5,599,345 A | 2/1997 | Edwards et al. |
| 5,267,994 A | 12/1993 | Gentelia et al. | 5,599,348 A | 2/1997 | Gentelia et al. |
| 5,267,997 A | 12/1993 | Farin | 5,605,150 A | 2/1997 | Radons et al. |
| 5,281,213 A | 1/1994 | Milder et al. | 5,613,966 A | 3/1997 | Makower et al. |
| 5,300,068 A | 4/1994 | Rosar et al. | 5,626,575 A | 5/1997 | Crenner |
| 5,300,070 A | 4/1994 | Gentelia | 5,628,745 A | 5/1997 | Bek |
| 5,318,563 A | 6/1994 | Malis et al. | 5,643,330 A | 7/1997 | Holsheimer et al. |
| 5,323,778 A | 6/1994 | Kandarpa et al. | 5,647,869 A | 7/1997 | Goble et al. |
| 5,324,283 A | 6/1994 | Heckele | 5,647,871 A | 7/1997 | Levine et al. |
| 5,330,518 A | 7/1994 | Neilson et al. | 5,651,780 A | 7/1997 | Jackson et al. |
| 5,334,183 A | 8/1994 | Wuchinich | 5,658,322 A | 8/1997 | Fleming |
| 5,334,193 A | 8/1994 | Nardella | 5,660,567 A | 8/1997 | Nierlich et al. |
| 5,341,807 A | 8/1994 | Nardella | 5,674,217 A | 10/1997 | Wahlstrom et al. |
| 5,342,356 A | 8/1994 | Ellman | 5,685,840 A | 11/1997 | Schechter et al. |
| 5,342,357 A | 8/1994 | Nardella | 5,688,267 A | 11/1997 | Panescu et al. |
| 5,342,409 A | 8/1994 | Mullett | 5,693,042 A | 12/1997 | Bioarski et al. |
| 5,348,554 A | 9/1994 | Imran et al. | 5,694,304 A | 12/1997 | Telefus et al. |
| 5,370,645 A | 12/1994 | Klicek et al. | 5,695,494 A | 12/1997 | Becker |
| 5,370,672 A | 12/1994 | Fowler et al. | 5,696,441 A | 12/1997 | Mak et al. |
| 5,370,675 A | 12/1994 | Edwards et al. | 5,702,386 A | 12/1997 | Stern et al. |
| 5,372,596 A | 12/1994 | Klicek et al. | 5,702,429 A | 12/1997 | King |
| 5,383,874 A | 1/1995 | Jackson | 5,707,369 A | 1/1998 | Vaitekunas et al. |
| 5,383,876 A | 1/1995 | Nardella | 5,712,772 A | 1/1998 | Telefus et al. |
| 5,383,917 A | 1/1995 | Desai et al. | 5,713,896 A | 2/1998 | Nardella |
| 5,385,148 A | 1/1995 | Lesh et al. | 5,718,246 A | 2/1998 | Vona |
| 5,400,267 A | 3/1995 | Denen et al. | 5,720,744 A | 2/1998 | Eggleston et al. |
| 5,403,311 A | 4/1995 | Abele et al. | 5,722,975 A | 3/1998 | Edwards et al. |
| 5,403,312 A | 4/1995 | Yates et al. | 5,729,448 A | 3/1998 | Haynie et al. |
| 5,409,000 A | 4/1995 | Imran | 5,733,281 A | 3/1998 | Nardella |
| 5,409,485 A | 4/1995 | Suda | 5,749,869 A | 5/1998 | Lindenmeier et al. |
| 5,413,573 A | 5/1995 | Koivukangas | 5,749,871 A | 5/1998 | Hood et al. |
| 5,414,238 A | 5/1995 | Steigerwald et al. | 5,755,715 A | 5/1998 | Stern |
| 5,417,719 A | 5/1995 | Hull et al. | 5,766,165 A | 6/1998 | Gentelia et al. |
| 5,422,567 A | 6/1995 | Matsunaga | 5,769,847 A | 6/1998 | Panescu |
| 5,423,808 A | 6/1995 | Edwards et al. | 5,772,659 A | 6/1998 | Becker et al. |
| 5,423,809 A | 6/1995 | Klicek | 5,792,138 A | 8/1998 | Shipp |
| 5,423,810 A | 6/1995 | Goble et al. | 5,797,902 A | 8/1998 | Netherly |
| 5,425,704 A | 6/1995 | Sakurai et al. | 5,814,092 A | 9/1998 | King |
| 5,430,434 A | 7/1995 | Lederer et al. | 5,817,093 A | 10/1998 | Williamson, IV et al. |
| 5,432,459 A | 7/1995 | Thompson | 5,820,568 A | 10/1998 | Willis |
| 5,433,739 A | 7/1995 | Sluijter et al. | 5,827,271 A | 10/1998 | Bussey et al. |
| 5,436,566 A | 7/1995 | Thompson | 5,830,212 A | 11/1998 | Cartmell |
| 5,438,302 A | 8/1995 | Goble | 5,836,909 A | 11/1998 | Cosmescu |
| 5,443,463 A | 8/1995 | Stern et al. | 5,836,943 A | 11/1998 | Miller, III |
| 5,445,635 A | 8/1995 | Denen | 5,836,990 A | 11/1998 | Li |

| | | | | | | |
|---|---|---|---|---|---|---|
| 5,846,236 | A | 12/1998 | Lindenmeier et al. | 6,337,998 B1 | 1/2002 | Behl et al. |
| 5,868,737 | A | 2/1999 | Taylor et al. | 6,338,657 B1 | 1/2002 | Harper et al. |
| 5,868,739 | A | 2/1999 | Lindenmeier et al. | 6,350,262 B1 | 2/2002 | Ashley |
| 5,868,740 | A | 2/1999 | LeVeen et al. | 6,358,245 B1 | 3/2002 | Edwards |
| 5,871,481 | A | 2/1999 | Kannenberg et al. | 6,364,877 B1 | 4/2002 | Goble et al. |
| 5,897,552 | A | 4/1999 | Edwards et al. | 6,383,183 B1 | 5/2002 | Sekino et al. |
| 5,908,444 | A | 6/1999 | Azure | 6,391,024 B1 | 5/2002 | Sun et al. |
| 5,913,882 | A | 6/1999 | King | 6,398,779 B1 | 6/2002 | Buysse et al. |
| 5,921,982 | A | 7/1999 | Lesh et al. | 6,398,781 B1 | 6/2002 | Goble et al. |
| 5,925,070 | A | 7/1999 | King et al. | 6,402,741 B1 | 6/2002 | Keppel et al. |
| 5,931,836 | A | 8/1999 | Hatta et al. | 6,402,742 B1 * | 6/2002 | Blewett et al. ............... 606/34 |
| 5,938,690 | A | 8/1999 | Law et al. | 6,402,743 B1 | 6/2002 | Orszulak et al. |
| 5,948,007 | A | 9/1999 | Starkenbaum et al. | 6,416,509 B1 | 7/2002 | Goble et al. |
| 5,951,545 | A | 9/1999 | Schilling | 6,436,096 B1 | 8/2002 | Hareyama |
| 5,951,546 | A | 9/1999 | Lorentzen | 6,451,015 B1 | 9/2002 | Rittman, III et al. |
| 5,954,686 | A | 9/1999 | Garito et al. | 6,458,121 B1 | 10/2002 | Rosenstock |
| 5,954,717 | A | 9/1999 | Behl et al. | 6,464,689 B1 | 10/2002 | Qin |
| 5,954,719 | A | 9/1999 | Chen et al. | 6,464,696 B1 | 10/2002 | Oyama |
| 5,961,344 | A | 10/1999 | Rosales et al. | 6,498,466 B1 | 12/2002 | Edwards |
| 5,971,980 | A | 10/1999 | Sherman | 6,506,189 B1 | 1/2003 | Rittman, III et al. |
| 5,976,128 | A | 11/1999 | Schilling et al. | 6,508,815 B1 | 1/2003 | Strul |
| 5,983,141 | A | 11/1999 | Sluijter et al. | 6,511,476 B2 | 1/2003 | Hareyama |
| 6,010,499 | A | 1/2000 | Cobb | 6,511,478 B1 | 1/2003 | Burnside et al. |
| 6,014,581 | A | 1/2000 | Whayne et al. | 6,517,538 B1 | 2/2003 | Jacob et al. |
| 6,033,399 | A | 3/2000 | Gines | 6,524,308 B1 | 2/2003 | Muller et al. |
| 6,044,283 | A | 3/2000 | Fein et al. | 6,547,786 B1 | 4/2003 | Goble |
| 6,053,910 | A | 4/2000 | Fleenor | 6,558,376 B2 | 5/2003 | Bishop |
| 6,053,912 | A | 4/2000 | Panescu et al. | 6,560,470 B1 | 5/2003 | Pologe |
| 6,055,458 | A | 4/2000 | Cochran et al. | 6,562,037 B2 | 5/2003 | Paton |
| 6,056,745 | A | 5/2000 | Panescu et al. | 6,565,559 B2 | 5/2003 | Eggleston |
| 6,056,746 | A | 5/2000 | Goble et al. | 6,575,969 B1 | 6/2003 | Rittman, III et al. |
| 6,063,075 | A | 5/2000 | Mihori | 6,582,427 B1 | 6/2003 | Goble et al. |
| 6,063,078 | A | 5/2000 | Wittkampf | 6,620,157 B1 | 9/2003 | Dabney et al. |
| 6,068,627 | A | 5/2000 | Orszulak et al. | 6,623,423 B2 | 9/2003 | Sakurai et al. |
| 6,074,386 | A | 6/2000 | Goble et al. | 6,629,973 B1 | 10/2003 | Wardell et al. |
| 6,074,388 | A | 6/2000 | Tockweiler et al. | 6,635,057 B2 | 10/2003 | Harano |
| 6,080,149 | A | 6/2000 | Huang et al. | 6,645,198 B1 | 11/2003 | Bommannan et al. |
| 6,093,186 | A | 7/2000 | Goble | 6,648,883 B2 | 11/2003 | Francischelli |
| 6,102,497 | A | 8/2000 | Ehr et al. | 6,652,514 B2 | 11/2003 | Ellman |
| 6,113,591 | A | 9/2000 | Whayne et al. | 6,663,623 B1 | 12/2003 | Oyama et al. |
| 6,113,596 | A | 9/2000 | Hooven | 6,663,624 B2 | 12/2003 | Edwards |
| 6,123,702 | A | 9/2000 | Swanson et al. | 6,666,860 B1 | 12/2003 | Takahashi |
| 6,132,429 | A | 10/2000 | Baker | 6,679,875 B2 | 1/2004 | Honda |
| 6,142,992 | A | 11/2000 | Cheng et al. | 6,682,527 B2 | 1/2004 | Strul |
| 6,155,975 | A | 12/2000 | Urich et al. | 6,685,700 B2 | 2/2004 | Behl |
| 6,162,217 | A | 12/2000 | Kannenberg et al. | 6,685,701 B2 | 2/2004 | Orszulak et al. |
| 6,171,304 | B1 | 1/2001 | Netherly et al. | 6,685,703 B2 | 2/2004 | Pearson et al. |
| 6,188,211 | B1 | 2/2001 | Rincon-Mora et al. | 6,689,131 B2 | 2/2004 | McClurken |
| 6,203,541 | B1 | 3/2001 | Keppel | 6,692,489 B1 | 2/2004 | Heim |
| 6,210,403 | B1 | 4/2001 | Klicek | 6,693,782 B1 | 2/2004 | Lash |
| 6,222,356 | B1 | 4/2001 | Taghizadeh-Kaschani | 6,712,813 B2 | 3/2004 | Ellman |
| 6,228,080 | B1 | 5/2001 | Gines | 6,730,080 B2 | 5/2004 | Harano |
| 6,228,081 | B1 | 5/2001 | Goble | 6,733,495 B1 | 5/2004 | Bek |
| 6,231,569 | B1 | 5/2001 | Bek | 6,733,498 B2 | 5/2004 | Paton |
| 6,235,020 | B1 | 5/2001 | Cheng et al. | 6,740,079 B1 | 5/2004 | Eggers |
| 6,238,387 | B1 | 5/2001 | Miller, III | 6,740,085 B2 | 5/2004 | Hareyama |
| 6,238,388 | B1 | 5/2001 | Ellman | 6,755,825 B2 | 6/2004 | Shoenman et al. |
| 6,241,725 | B1 | 6/2001 | Cosman | 6,758,846 B2 | 7/2004 | Goble et al. |
| 6,245,065 | B1 | 6/2001 | Panescu | 6,783,523 B2 | 8/2004 | Qin |
| 6,246,912 | B1 | 6/2001 | Sluijter et al. | 6,786,905 B2 | 9/2004 | Swanson et al. |
| 6,251,106 | B1 | 6/2001 | Becker et al. | 6,790,206 B2 | 9/2004 | Panescu |
| 6,258,085 | B1 | 7/2001 | Eggleston | 6,796,981 B2 | 9/2004 | Wham |
| 6,261,285 | B1 | 7/2001 | Novak | 6,824,539 B2 | 11/2004 | Novak |
| 6,261,286 | B1 | 7/2001 | Goble et al. | 6,830,569 B2 | 12/2004 | Thompson |
| 6,273,886 | B1 | 8/2001 | Edwards | 6,843,789 B2 | 1/2005 | Goble |
| 6,275,786 | B1 | 8/2001 | Daners | 6,849,073 B2 | 2/2005 | Hoey |
| 6,293,941 | B1 | 9/2001 | Strul | 6,855,141 B2 | 2/2005 | Lovewell |
| 6,293,942 | B1 | 9/2001 | Goble et al. | 6,855,142 B2 | 2/2005 | Harano |
| 6,296,636 | B1 | 10/2001 | Cheng et al. | 6,860,881 B2 | 3/2005 | Sturm |
| 6,306,131 | B1 | 10/2001 | Hareyama et al. | 6,864,686 B2 | 3/2005 | Novak |
| 6,306,134 | B1 | 10/2001 | Goble et al. | 6,875,210 B2 | 4/2005 | Refior |
| 6,309,386 | B1 | 10/2001 | Bek | 6,893,435 B2 | 5/2005 | Goble |
| 6,325,799 | B1 | 12/2001 | Goble | 6,923,804 B2 | 8/2005 | Eggers et al. |

| | | |
|---|---|---|
| 6,929,641 B2 | 8/2005 | Goble et al. |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,966,907 B2 | 11/2005 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,381 B2 | 2/2006 | Harano et al. |
| 7,004,174 B2 | 2/2006 | Eggers et al. |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,122,031 B2 | 10/2006 | Edwards et al. |
| 7,131,860 B2 | 11/2006 | Sartor et al. |
| 7,137,980 B2 | 11/2006 | Buysse et al. |
| 7,147,638 B2 | 12/2006 | Chapman et al. |
| 7,160,293 B2 | 1/2007 | Sturm et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,211,081 B2 | 5/2007 | Goble |
| 7,214,224 B2 | 5/2007 | Goble |
| 7,220,260 B2 | 5/2007 | Fleming et al. |
| 7,247,155 B2 | 7/2007 | Hoey et al. |
| 7,250,746 B2 | 7/2007 | Oswald et al. |
| 7,255,694 B2 | 8/2007 | Keppel |
| 7,282,048 B2 | 10/2007 | Goble et al. |
| 7,300,435 B2 | 11/2007 | Wham et al. |
| 7,303,557 B2 | 12/2007 | Wham et al. |
| 7,364,577 B2 | 4/2008 | Wham et al. |
| 7,367,972 B2 | 5/2008 | Francischelli et al. |
| RE40,388 E | 6/2008 | Gines |
| 7,396,336 B2 | 7/2008 | Orszulak et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Flemming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1* | 7/2007 | Orszulak ..................... 606/37 |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |

| | | |
|---|---|---|
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 0694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1645235 | 4/2006 |
| EP | 0880220 B1 | 6/2006 |
| EP | 1707143 | 10/2006 |
| EP | 1 810630 | 7/2007 |
| EP | 1810628 | 7/2007 |
| EP | 1810633 | 7/2007 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 1290304 * | 9/1972 |
| GB | 2164473 | 3/1986 |
| GB | 2214430 | 9/1989 |
| GB | 2358934 A | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/092520 | 11/2003 |
| WO | WO2003/090635 | 11/2003 |
| WO | WO2004/028385 | 4/2004 |
| WO | WO2004/098385 | 4/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO05048809 A1 | 6/2005 |
| WO | WO2005/060365 | 7/2005 |
| WO | WO2005/060849 | 7/2005 |

OTHER PUBLICATIONS

International Search Report-Extended EP 06000708.5 dated Aug. 22, 2006.
International Search Report EP 05002769.7, dated Jun. 9, 2006.
International Search Report EP 06006717.0 dated Aug. 7, 2006.
Ni W et al: "A Signal Processing Method for the Coriolis Mass Flowmeter Based on a Normalized . . ." Journal of Applied Sciences-Yingyong Kexue Xuebao, Shanghai CN, vol. 23 No. 2;(Mar. 2005); 160-164.
Alexander et al., "Magnetic Resonance Image-Directed Stereotactic Neurosurgery: Use of Image Fusion with Computerized Tomography to Enhance Spatial Accuracy". Journal Neurosurgery. 83: (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan. " A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith", Aug. 1996, pp. 283-297 Signal Processing. Elsevier Science Publishers B.V. Amsterdam, NL vol. 52 No. 3.
Cosman et al., "Methods of Making Nervous System Lesion" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman at al., "Theoretical Aspects of Radiofrequency Lesions in the Dorsal Root Entry Zone" Neurosurgery 15:(1984) pp. 945-950.
Geddes et al , "The Measurement of Physiologic Events by Electrical Impedence" Am J MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p Sep. 1998.
Ogden, Goertzel Alternative to the Fourier Transform: Jun. 1993 pp. 485-487 Electronics World; Reed Business Publishing, Sutton, Surrey, BG vol. 99, No. 9, 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp Nov. 1995.
Vallfors et al. "Automatically Controlled Bipolar Electrosoagulation-'COA-COMP"Neurosurgical Review 7:2-3 (1984) pp. 187-190.
Wald et al, "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.

International Search Report EP 04015981.6 dated Sep. 29, 2004.
International Search Report EP 05014156.3 dated Dec. 28, 2005.
International dated Search Report EP 05021944.3 dated Jan. 18, 2006.
International Search Report EP 05022350.2 dated Jan. 18, 2006.
International Search Report EP 07008207.8; dated Sep. 5, 2007.
International Search Report EP 07010673.7; dated Sep. 24, 2007.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.

* cited by examiner

SYSTEM AND METHOD FOR GENERATING RADIO FREQUENCY ENERGY

BACKGROUND

1. Field

The present disclosure relates generally to electrosurgical systems and, more specifically, to a system for delivering high power radiofrequency energy using multiple resonant inductor-capacitor (LC) networks.

2. Description of the Related Art

Electrosurgery involves application of high radio frequency (RF) electrical energy to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is a monopolar procedure which is particularly useful in the field of neurosurgery, where one or more RF ablation needle electrodes (usually of elongated cylindrical geometry) are inserted into a living body. A typical form of such needle electrodes incorporates an insulated sheath from which an exposed (uninsulated) tip extends. When an RF voltage is provided between the reference electrode and the inserted ablation electrode, RF current flows from the needle electrode through the body. Typically, the current density is very high near the tip of the needle electrode, which heats and destroys the adjacent tissue.

In bipolar electrosurgery, one of the electrodes of the hand-held instrument functions as the active electrode and the other as the return electrode. The return electrode is placed in close proximity to the active (current supplying) electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

In electrosurgery, RF energy must be generated having sufficient frequency, so that the RF energy may be used to cut, coagulate, etc., tissue by sustaining tissue thermal heating for prolonged periods of time. Current state of the art electrosurgical generators do not provide sufficiently powerful RF energy for prescribed periods of time or they do so in an inefficient manner. Therefore there is a need for an electrosurgical generator which can generate high amounts electrosurgical energy in an efficient manner.

SUMMARY

The present disclosure provides for an electrosurgical generator that includes an RF output stage connected to a DC power supply. The RF output stage includes two connections that receive DC energy and are connected to a transformer. Each of the two connections include a switching component that are cycled between on and off positions at the same frequency but in a 180 degree out-of-phase relationship and a parallel inductor-capacitor resonant circuit. The two connections also include a series inductor-capacitor resonant circuit oriented at a primary winding of the transformer. The first connection generates a positive half-sinusoidal waveform and the second connection generates a 180° phase-shifted positive half-sinusoidal waveform. The waveforms combine at the transformer to form a pure sine output waveform suitable for electrosurgical procedures involving RF energy.

According to one embodiment of the present disclosure, an electrosurgical generator is disclosed. The electrosurgical generator includes a power supply for generating a DC voltage. The electrosurgical generator also includes a first parallel inductor-capacitor circuit being driven by a first signal at a first predetermined frequency and a second parallel inductor-capacitor inductor-capacitor circuit driven by a second signal at the first predetermined frequency phase shifted 180°. The electrosurgical generator further includes a series inductor-capacitor resonant circuit operably connected in series with a primary winding of a transformer. The first and second parallel inductor-capacitor circuits are operably connected to the transformer, such that the first inductor-capacitor circuit generates a positive half sine wave and the second inductor-capacitor circuit generates a 180° phase-shifted positive half sine wave to generate a full sine wave in a secondary winding of the transformer.

According to another aspect of the present disclosure, a method for generating high frequency electrosurgical current is disclosed. The method includes the step of providing a power supply operable to generate a DC voltage, a first parallel inductor-capacitor circuit, a second parallel inductor-capacitor circuit, a series inductor-capacitor resonant circuit. The first parallel inductor-capacitor circuit, the second parallel inductor-capacitor circuit, and the series inductor-capacitor resonant circuit are operably connected in series with a primary winding of a transformer. The method also includes the steps of driving a first parallel inductor-capacitor circuit by a first signal at a first predetermined frequency. The method also includes the step of driving a second parallel inductor-capacitor inductor-capacitor circuit by a second signal at the first predetermined frequency phase-shifted 180°. The method further includes the steps of generating a positive half sine wave at the first inductor-capacitor parallel circuit, generating a 180° phase-shifted positive half sine wave at the second parallel inductor-capacitor circuit, and combining the positive half sine wave and the 180° phase-shifted positive half sine wave at the secondary winding of the transformer to generate a full sine wave.

According to a further aspect of the present disclosure a radio frequency (RF) output stage circuit is disclosed. The RF output stage circuit includes a first parallel inductor-capacitor circuit configured to generate a positive half sine wave driven by a first signal at a first predetermined frequency. The first parallel inductor-capacitor circuit being operably connected to a transformer which includes a first winding and a series inductor-capacitor resonant circuit connected in series to a second winding. The RF output stage circuit also includes a second parallel inductor-capacitor circuit configured to generate a 180° phase-shifted positive half sine wave driven by a second signal at the first predetermined frequency phase-shifted 180°. The second parallel inductor-capacitor circuit is operably connected to the transformer such that the positive half sine wave and the 180° phase-shifted positive half sine wave are combined at the secondary winding of the transformer to generate a full sine wave.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Preferred embodiments of the present disclosure are described below with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar, ablation or bipolar electrosurgical systems.

Figure 1:
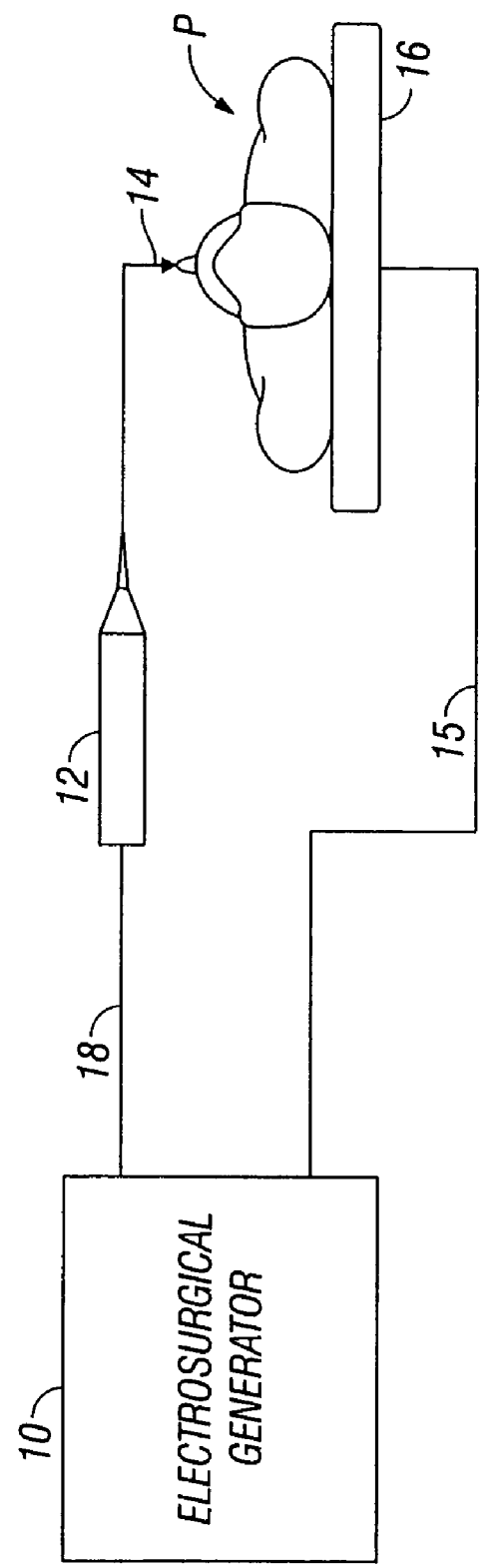
FIG. 1 is a schematic block diagram of one embodiment of an electrosurgical system according to the present disclosure.

FIG. 1 is a schematic illustration of a monopolar electrosurgical system. The system includes an active electrode 14 and a return electrode 16 for treating tissue of a patient P. Electrosurgical RF energy is supplied to the active electrode 14 by a generator 10 via a cable 18 allowing the active electrode 14 to ablate, cut or coagulate the tissue. The return electrode 16 is placed at the patient P to return the energy from the patient P to the generator 10 via a cable 15.

The generator 10 includes similar input controls (e.g., buttons, activators, switches, etc.) for controlling the generator 10. The controls allow the surgeon to adjust power of the RF energy, waveform, and other parameters to achieve the desired waveform suitable for a particular task (e.g., cutting, coagulating, etc.). Disposed between the generator 10 and the active electrode 14 on the cable 18 is a hand piece 12, which includes a plurality of input controls that may be redundant with certain input controls of the generator 10. Placing the input controls at the hand piece 12 allows for easier and faster modification of RF energy parameters during the surgical procedure without returning to the generator 1. Active electrode 14 may include a temperature sensor, such as a thermocouple, for sensing temperature at or approximate the surgical site. The temperature sensor wires may be disposed in cable 18.

Figure 2:
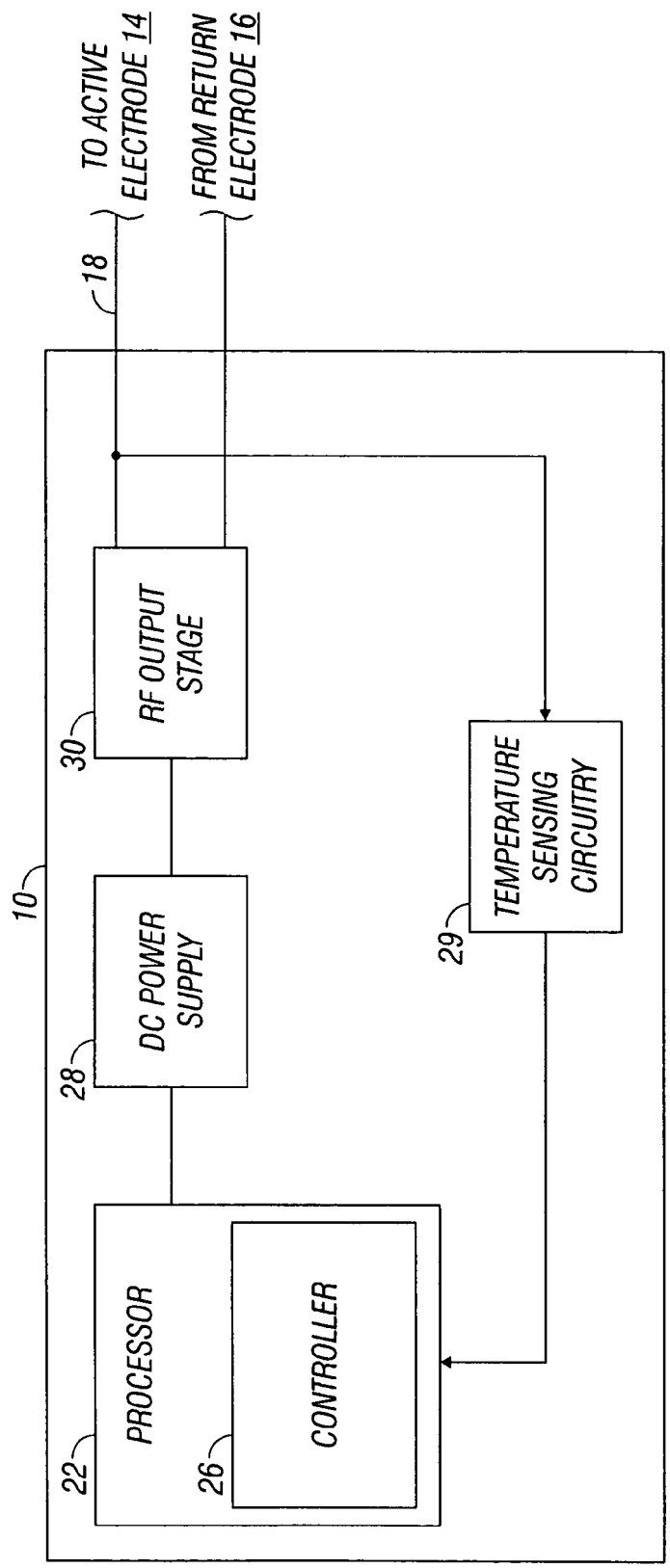
FIG. 2 is a schematic block diagram of a generator according to the present disclosure.

FIG. 2 shows a schematic block diagram of the generator 10 having a microprocessor 22, a high voltage DC power supply 28, and an RF output stage 30. The microprocessor 22 includes a controller 26 and an output port that is electrically connected to the DC power supply 28 configured to supply DC power to the RF output stage 30. The microprocessor 22 receives input signals from the generator 10 and/or hand piece 12 and the controller 26 in turn adjusts power outputted by the generator 10, more specifically the DC power supply 28, and/or performs other control functions thereon. Furthermore, the generator 10 may include temperature circuitry 29 for determining the temperature at the surgical site, which may adjust the power outputted by the generator 10.

Figure 3:
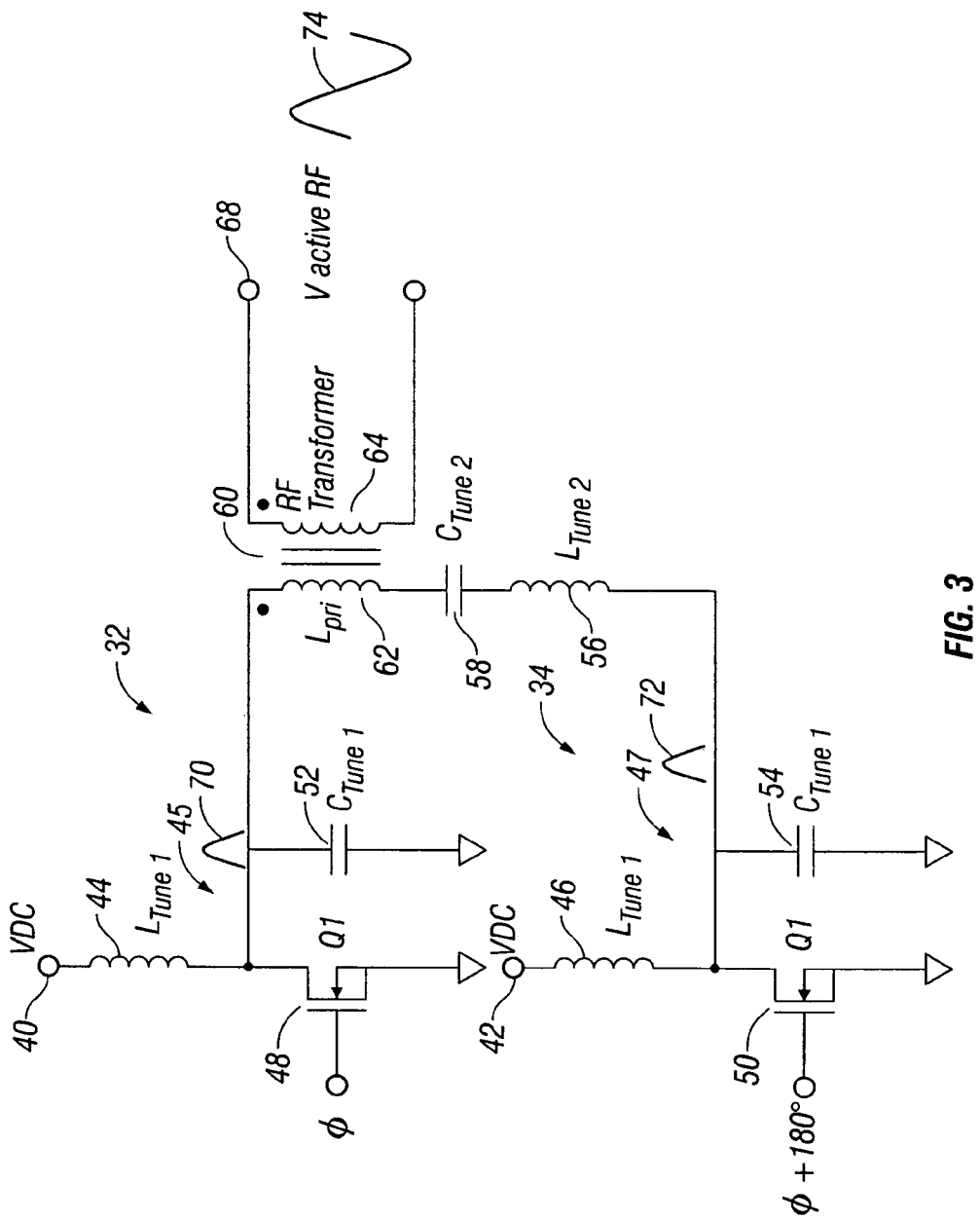
FIG. 3 is a circuit diagram of a radio frequency (RF) output stage according to the present disclosure.

The RF output stage 30 converts DC power into RF energy and delivers the RF energy to the active electrode 14. In addition, the RF output stage 30 also receives RF energy from the return electrode 16. As shown in more detail in FIG. 3, the RF output stage 30 receives DC voltage from the DC power supply 28 at inputs 40, 42, wherein first and second connections 32, 34 of a first winding 62 of a transformer 60 create two half-sinusoidal waveforms 180° out-of-phase, which then combine at a secondary winding 64 of the transformer 60 to form a pure (e.g., full) sinusoidal waveform.

The power of the DC power supply 28 can be varied to modify RF magnitude (e.g., amplitude) thereby adjusting the power of the RF energy delivered to the tissue. This allows for accurate regulation of the power of delivered RF energy.

The first and second connections 32, 34 include switching components 48, 50 and parallel inductor-capacitor resonant circuits 45, 47 (parallel LC circuits 45, 47), respectively. The switching components 48, 50 may be, for example, transistors, such as metal-oxide semiconductor field-effect transistors (MOSFET), insulated gate bipolar transistors (IGBT), and relays. The switching components 48, 50 are turned on and off at a predetermined frequency which is also the operating frequency of the generator 10, thereby closing and opening the first and second connections 32, 34, respectively. The frequency at which the switching components 48, 50 are turned on and off is controlled by a driver (not explicitly shown). The driver emits a phase-correlated (e.g., the switching components 48, 50 have a phase relationship) dual drive signal (e.g., $\phi$ and $\phi\_180°$). More simply put, the driver signal cycles the switching components 48, 50 between on and off positions at the same frequency but out of sync, to create two half-sinusoidal sinusoidal waveforms 180° out-of-phase. Therefore, adjusting the phase-correlated dual drive signal provides a means for varying operating RF frequency. Pulsing of the phase-correlated dual drive signal also provides means for RF duty cycle control.

Each of the first and second connections 32, 34 includes the parallel LC circuits 45, 47, respectively, which convert DC electrical energy into RF energy, such as AC energy having high frequency 300 kHz-1000 kHz. The parallel LC circuits 45, 47 include inductors 44, 46 connected in parallel with first capacitors 52, 54 respectively. When the switching components 48, 50 are closed, DC power is supplied to the inductors 44, 46, which thereafter discharge through the first capacitors 52, 54 respectively, when the switching components 48, 50 are open. This process converts the constant pulse of DC energy into half-sinusoidal waveforms 70, 72 by the first and second connections 32, 34, respectively. Since the switching components 48, 50 turn on and off at the same frequency but 180° out-of-phase, the resulting half-sinusoidal waveforms 70, 72 are also 180° out-of-phase.

The first and second connections 32, 34 also include a series inductor-capacitor (LC) resonant circuit 57 which includes an inductor 56 and a capacitor 58 oriented on the second connection 34 of the primary winding 62. The series LC circuit 57 and the parallel LC circuits 45, 47 have a dissimilar resonant operating frequency. The series LC circuit 57 is preferably within 200 kHz of the operating frequency, which is 280 kHz. The parallel resonant LC circuits 45, 47 are preferably within 80 kHz of the operating frequency which is preferably 544 kHz. The resonant frequency is based on the inductance and capacitance values of the series LC circuit 57 and the parallel LC circuits 45, 47 preferably, the inductance of the inductors 44, 46, 56 and capacitance of the capacitors 52, 54, 58 are selected which maximize the RF power developed for performing medical procedures. Inductors 44, 46 may be 14 µhγ each, the inductor 56 may be 12.5 µhγ. Capacitors 52, 54 may be 0.011 µf and capacitor 58 is 0.0183 µf. The primary winding 62 and inductance contribute to the series and parallel resonant LC tune and is further optimized dependent of the RF energy to be delivered by the transformer 60.

Figure 4A:
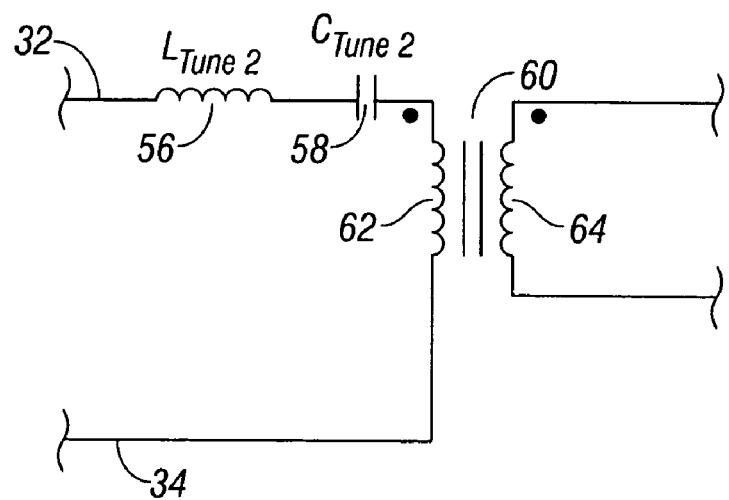
FIGS. 4A-D are circuit diagrams of alternate embodiments of the RF output stage according to the present disclosure.
Figure 4B:
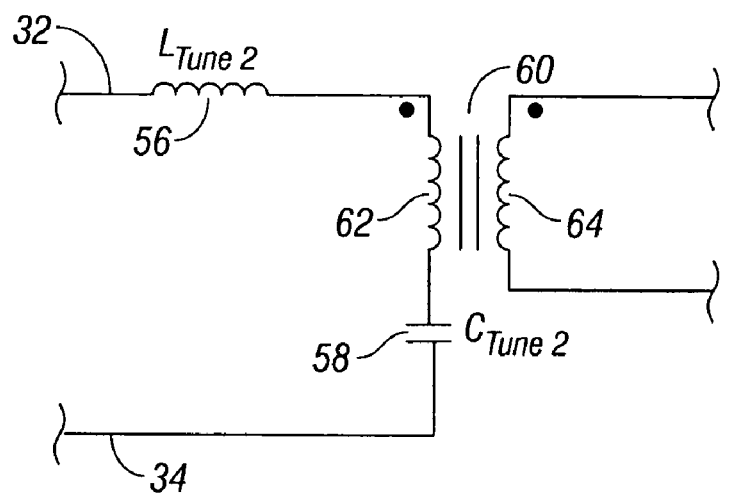
Figure 4C:
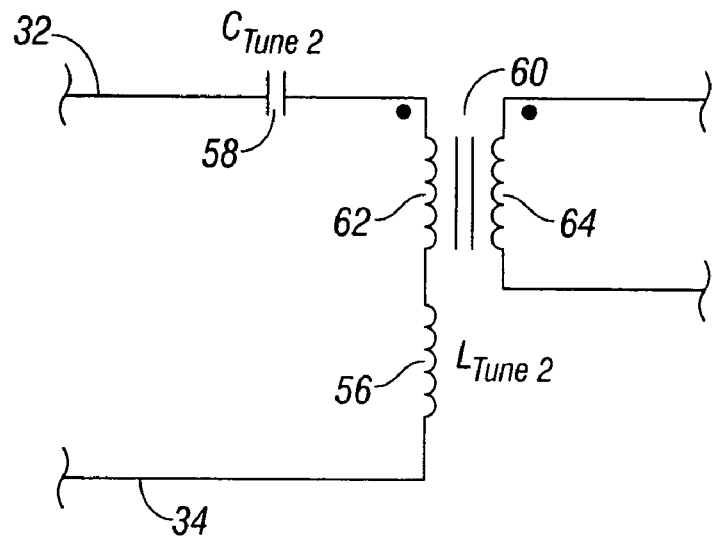
Figure 4D:
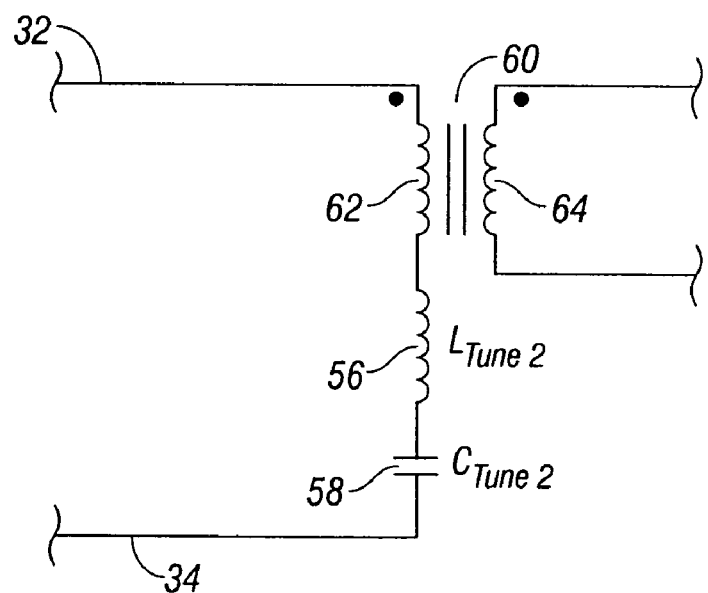

Shown in FIGS. 4A-D are alternate orientations of the inductor 56 and the capacitor 58. The alternate orientations have no effect on the functionality of the first and second connections 32, 34. As shown in FIG. 4A, the inductor 56 and the capacitor 58 are oriented on first connection 32, with the capacitor 58 oriented between the primary winding 62 and the inductor 56. As shown in FIGS. 4B, the capacitor 58 is oriented on the second connection 34 and the inductor 56 is oriented on the first connection 32. As shown in FIGS. 4C, the capacitor 58 is oriented on the first connection 32 and the inductor 56 is oriented on the second connection 34. FIG. 4D shows the inductor 56 and the capacitor 58 oriented on the second connection 34, with the inductor 56 oriented between the primary winding 62 and the capacitor 58.

As discussed above, the switching components 48, 50 are alternately switched on and off at the same frequency by the phase correlated dual drive signal. This synchronizes the parallel LC circuits 45, 47 and the series LC circuit 57 and develops the half-sinusoidal waveforms 70, 72. The half-sinusoidal waveform 70 is magnetically coupled through the transformer 60 to develop a positive half-sine voltage to a patient-connective side 68 leading to the active electrode 14. The half-sinusoidal waveform 72 is coupled through the transformer 60 to develop a negative half-sine voltage. The half-sinusoidal waveforms 70, 72 combine on the secondary winding 64 (e.g., the patient-connective side 68) to generate a pure sine wave 74 because the half-sinusoidal waveforms 70, 72 are 180° out-of-phase.

Embodiments of the present disclosure provide for an electrosurgical generator that includes coupled series and parallel resonant LC networks. The LC networks permit development of high RF power without sacrificing high efficiency. More specifically, the efficiency is due to the reduced power loss of the coupled LC resonant topology, which minimizes the need for additional heat removal associated with high power RF energy generation processes. The dual resonant topology, with combined series and parallel LC resonant circuit provides efficient energy transfer between reactive LC components which consume minimal power loss. The only losses occur as a result of the conductivity losses of the transistors. There are no switching losses, since the voltage across the transistors is zero at the time they are activated. By definition, reactive components the inductors and capacitors in the LC circuits do not dissipate real power, which allows for high efficiency. The LC network generates less heat as a result of the reactive impedance compared to the real power loss associated with resistive elements. Use of efficient LC resonant energy storage system also allows for a reduction in weight and form factor for a given power level.

In addition, the generator may provide increasing lesion creation capability, more specifically, the generator allows for creation of larger ablation volumes in tissue. In particular, larger lesions require significantly more power (i.e., power requirements increase exponentially with lesion size). The generator according to the present disclosure is capable of forming lesions of diameters 8 cm or larger due to the efficiency of its power output.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical generator comprising:
   a power supply operable to generate a DC voltage;
   a first parallel inductor-capacitor circuit configured to be driven by a first signal at a first predetermined frequency;
   a second parallel inductor-capacitor circuit configured to be driven by a second signal at the first predetermined frequency phase-shifted 180°;
   a series inductor-capacitor resonant circuit operably connected in series with a primary winding of a transformer, the first and second parallel inductor-capacitor circuits operably connected to the transformer, the first parallel inductor-capacitor circuit being configured to generate a positive half sine wave from the DC voltage and the second parallel inductor-capacitor circuit being configured to generate a 180° phase-shifted positive half sine wave from the DC voltage to generate a full sine wave in a secondary winding of the transformer; and
   a temperature circuit configured to determine temperature at a surgical site and adjust the DC voltage generated by the power supply.

2. An electrosurgical generator as in claim 1, wherein the first parallel inductor-capacitor resonant circuit is tuned to a first self-resonant frequency that is substantially equivalent to the first predetermined frequency.

3. An electrosurgical generator as in claim 2, wherein the first parallel inductor-capacitor resonant circuit includes a first inductor having a first inductance value and a first capacitor having a first capacitance value, wherein the first inductance value and the first capacitance correspond to the first self-resonant frequency.

4. An electrosurgical generator as in claim 1, wherein the second parallel inductor-capacitor resonant circuit is tuned to a second self-resonant frequency that is substantially equivalent to the first predetermined frequency.

5. An electrosurgical generator as in claim 4, wherein the second parallel inductor-capacitor resonant circuit includes a second inductor having a second inductance value and a second capacitor having a second capacitance value, wherein the second inductance value and the second capacitance correspond to the second self-resonant frequency.

6. An electrosurgical generator as in claim 1, wherein the first and second parallel inductor-capacitor circuit are driven by switching on and off first and second switching components respectively.

7. An electrosurgical generator as in claim 6, wherein the first and second switching components are selected from the group consisting of transistors, relays, metal-oxide semiconductor field-effect transistors and insulated gate bipolar transistors.

8. An electrosurgical generator as in claim 1, wherein the series inductor-capacitor resonant circuit is tuned to a third self-resonant frequency that is substantially equivalent to the predetermined frequency.

9. An electrosurgical generator as in claim 8, wherein the series inductor-capacitor resonant circuit includes a third inductor having a third inductance value and a third capacitor having a third capacitance value, wherein the third inductance value and the third capacitance correspond to the third self-resonant frequency.

10. An electrosurgical generator as in claim 1, wherein temperature is sensed proximate the surgical site by a temperature sensor disposed on a remote electrode.

11. A method for generating high frequency electrosurgical current comprising the steps of:
   providing a power supply operable to generate a DC voltage, a first parallel inductor-capacitor circuit, a second parallel inductor-capacitor circuit, a series inductor-capacitor resonant circuit, wherein the first parallel inductor-capacitor circuit, the second parallel inductor-capacitor circuit, the series inductor-capacitor resonant circuit are operably connected in series with a primary winding of a transformer, and a temperature circuit configured to determine temperature at a surgical site and adjust the DC voltage generated by the power supply;

driving the first parallel inductor-capacitor circuit by a first signal at a first predetermined frequency;

driving the second parallel inductor-capacitor circuit by a second signal at the first predetermined frequency phase-shifted 180°; and generating a positive half sine wave at the first inductor-capacitor parallel circuit;

generating a 180° phase-shifted positive half sine wave at the second parallel inductor-capacitor circuit;

combining the positive half sine wave and the 180° phase-shifted positive half sine wave at a secondary winding of the transformer to generate a full sine wave; and determining temperature at the surgical site by the temperature circuit to adjust the DC voltage generated by the power supply.

12. A method as in claim 11, wherein the first parallel inductor-capacitor resonant circuit of the providing step is tuned to a first self-resonant frequency that is substantially equivalent to the first predetermined frequency.

13. A method as in claim 12, wherein the first parallel inductor-capacitor resonant circuit of the providing step includes a first inductor having a first inductance value and a first capacitor having a first capacitance value, wherein the first inductance value and the first capacitance correspond to the first self-resonant frequency.

14. A method as in claim 11, wherein the second parallel inductor-capacitor resonant circuit of the providing step is tuned to a second self-resonant frequency that is substantially equivalent to the first predetermined frequency.

15. A method as in claim 14, wherein the second parallel inductor-capacitor resonant circuit includes a second inductor having a second inductance value and a second capacitor having a second capacitance value, wherein the second inductance value and the second capacitance correspond to the second self-resonant frequency.

16. A method as in claim 11, wherein the first and second parallel inductor-capacitor circuits of the providing step are each driven in the respective driving steps by switching on and off first and second switching components respectively.

17. A method as in claim 16, wherein the first and second switching components are selected from the group consisting of transistors, relays, metal-oxide semiconductor field-effect transistors and insulated gate bipolar transistors.

18. A method as in claim 11, wherein the series inductor-capacitor resonant circuit of the providing step is tuned to a third self-resonant frequency that is substantially equivalent to the predetermined frequency.

19. A method as in claim 18, wherein the series inductor-capacitor resonant circuit of the providing step includes a third inductor having a third inductance value and a third capacitor having a third capacitance value, wherein the third inductance value and the third capacitance correspond to the third self-resonant frequency.

20. A method as in claim 11, wherein the temperature circuit of the determining step senses temperature proximate the surgical site by a temperature sensor disposed on a remote electrode.

\* \* \* \* \*